United States Patent [19]

Riggs et al.

[11] Patent Number: 5,711,916
[45] Date of Patent: Jan. 27, 1998

[54] AIR-TRANSPORTABLE MODULAR ANALYTICAL LABORATORY

[76] Inventors: Patti J. Riggs, 2116 Laurel Brook Rd., Fallston, Md. 21047; Monica J. Heyl, 9 Neptune Dr., Joppa, Md. 21085; Rodney D. Hudson, 1203 Schucks Rd., Bel Air, Md. 21015; Dennis J. Reutter, 2110 Brookhaven Ct., Fallston, Md. 21047

[21] Appl. No.: 657,433

[22] Filed: Jun. 3, 1996

Related U.S. Application Data

[63] Continuation of Ser. No. 326,338, Oct. 20, 1994, abandoned.
[51] Int. Cl.⁶ .................................................. G01N 30/02
[52] U.S. Cl. ...................... 422/83; 422/89; 422/104; 422/61; 220/630
[58] Field of Search ..................... 422/70, 68.1, 83, 422/61, 104, 89; 220/212, 630

[56] References Cited

U.S. PATENT DOCUMENTS

| | | | |
|---|---|---|---|
| 4,818,348 | 4/1989 | Sletter | 422/98 |
| 4,888,295 | 12/1989 | Zaromb et al. | 422/70 |
| 5,340,543 | 8/1994 | Annino et al. | 422/83 |

*Primary Examiner*—Lyle A. Alexander
*Attorney, Agent, or Firm*—Roland H. Shubert

[57] ABSTRACT

A modular analytical laboratory, that is air-transportable as commercial air freight, is provided. The laboratory includes an analytical module, a power module, and a service module that, when interconnected, form an independent, functioning laboratory capable of performing sophisticated chemical analyses. Each module includes a base upon which components are mounted, and a removable, protective cover that is adapted to serve as a module support when inverted.

11 Claims, 2 Drawing Sheets

AIR-TRANSPORTABLE MODULAR ANALYTICAL LABORATORY

This application of is a continuation application Ser. No. 08/326,338, filed Oct. 20, 1994, now abandoned.

The government has rights in this invention pursuant to Contract No. DAA 15-91-D-0019 awarded by Department of the Army.

TECHNICAL FIELD

This invention relates generally to transportable laboratories for the detection and quantification of contaminants in gas and liquid samples.

Specific embodiments of this invention include self-contained, modular, air transportable analytical laboratories utilizing fixed-lab quality, gas chromatographic and mass spectrographic techniques for detecting environmental contaminants.

BACKGROUND ART

There arises a pressing need for analytical capability whenever there is an uncontrolled release of dangerous contaminants into the environment. Such uncontrolled releases may result from accident, natural disaster, or the deliberate acts of man. For example, large quantities of dangerous chemicals are routinely transported by truck, rail and barge. There are occasional accidents during such transport, resulting in the rupture of containers or tanks, and the release of the contents. Tornados, hurricanes, and other severe storms can cause damage to manufacturing and storage facilities with the release of hazardous materials. Acts of war or terrorism have included the use of chemical agents, such as nerve gases and other poisons, as a weapon against an enemy.

In coping with such contaminant releases, it is ordinarily a first concern to determine the areal extent of the contamination and to monitor its spread. Thereafter, attention tends to focus on cleaning up or neutralizing the contamination. Both the determination of the extent of contamination and the supervision of cleanup activities usually requires sophisticated chemical analyses. It is common practice, in reacting to the release of a hazardous contaminant, to undertake a systematic program of sampling and analysis. The samples that are taken at the site are dispatched to a laboratory for analysis. It is often the case that the site of the contamination is remote from any laboratory competent to perform the required tests. That circumstance introduces delays that complicate remediation efforts, and may result in the unwitting exposure of personnel to unnecessary hazards.

A wide range of portable analytical devices have been developed, and those devices can sometimes serve as qualitative indicators of contamination. However, those portable devices often lack the sensitivity and discrimination necessary for safely managing releases of many of the more toxic contaminants, and offer little promise of supplanting the traditional laboratory.

There have been some efforts made in the field of chemical processing to provide modular work station elements that can be interchanged depending upon need. One such system is described in U.S. Pat. No. 4,345,615. Patentees provide a processing station having a frame capable of receiving multiple work modules, and supplying the utility needs of those modules. It is arranged such that each module may be interchanged with any other module, thus providing great processing flexibility to the system. Another example of a modular laboratory system incorporating fluid and electrical accessories and outlets is set out in the Propst et al patent, U.S. Pat. No. 3,920,299. The system comprises a free standing central core of at least two sub-frames, from which can be laterally cantilevered other laboratory components such as table tops.

In medicine, it is known to provide transportable carts containing all the equipment and supplies needed for a specific purpose. Examples of such systems include a wheeled, surgical case cart described in U.S. Pat. No. 4,550,986, and a mobile intensive care unit described in U.S. Pat. No. 5,007,688.

Despite the highly developed state of laboratory equipment in general, the art lacks self-contained and readily transportable means to provide sophisticated chemical analyses at remote sites.

DISCLOSURE OF THE INVENTION

This invention provides a totally self-contained, modular laboratory capable of carrying out sophisticated analyses at remote sites. The laboratory is arranged as a plurality of air-transportable modules that may be separated for transport but quickly interconnected for use. Each module includes a base adapted for lifting either by hand or by means of a fork lift, and upon which components are mounted. A removable, protective case including four sides and a top lockingly attaches to the base and forms a shipping container for the components mounted upon the base.

Accordingly, it is an object of this invention to provide a modular analytical laboratory that can be air-transported to a remote site and operated without dependence upon the local infrastructure.

Another object of this invention is to provide analytical services at remote sites for the determination of chemical contamination and the monitoring of remediation efforts.

Other objects will become apparent to one skilled in the art from the following description of various modes for carrying out the invention.

MODES FOR CARRYING OUT THE INVENTION

This invention provides a modular, totally self-contained, air transportable laboratory including all utilities and services required for operation. The laboratory comprises a plurality of modules arranged to be air transportable as commercial cargo without damage. Each module is arranged to be man-transportable, and includes one or more sub-systems. The components making up each sub-system are preferably identical to those that are used in a fixed laboratory environment for the same purpose. Together, the modules with their contained sub-systems interconnect to provide the required analytical capability.

The flexibility provided by the modular arrangement of the required sub-systems allows the laboratory to be operated in a variety of different configurations. Essentially all that needs to be provided at the operating site is protection from weather. That weather protection may be as simple as a tent or an abandoned building, or it may be comprise a cargo van or similar structure. A cargo van, for example, with little modification can provide on-site mobility to the laboratory. Laboratory modules may be rolled into the van, locked into place, and interconnected for use in performing the desired analyses. When no longer needed, the modules may then be removed from the van, and returned to their separate air-transportable configuration or used as the nucleus of a fixed and permanent laboratory.

Figure 1:
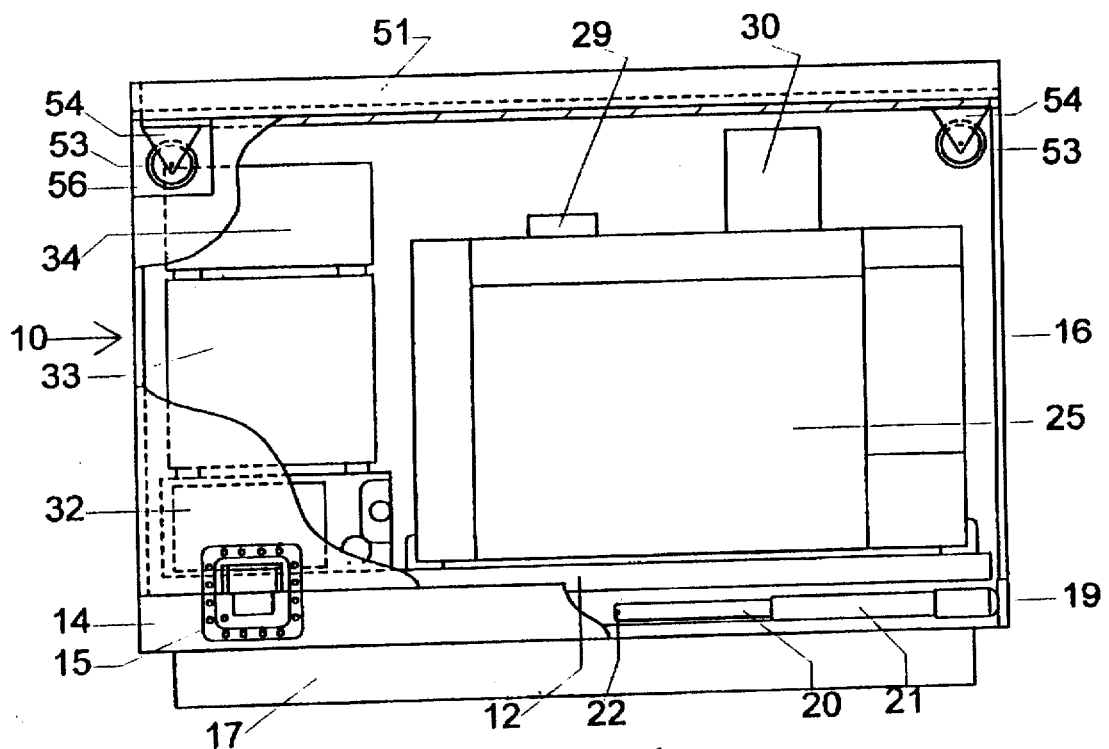
FIG. 1 is a partially broken away front view of an analytical module of this invention.

Various embodiments of the invention will be described and discussed in detail with reference to the drawing figures in which like reference numbers refer to the same component or part illustrated in the various figures. Referring first to FIG. 1, there is shown generally at 10 a partially broken away side view of an analytical module arranged according to this invention. The module includes a mounting plate 12 that is fixed upon base member 14. A removable, protective case 16 having an open bottom, closed side walls and a top, fits about plate 12 and rests upon base member 14. During transport and storage, case 16 is secured to member 14 through a plurality of locking hasps 15 that can be released to allow removal of the case 16 from the module.

Figure 2:
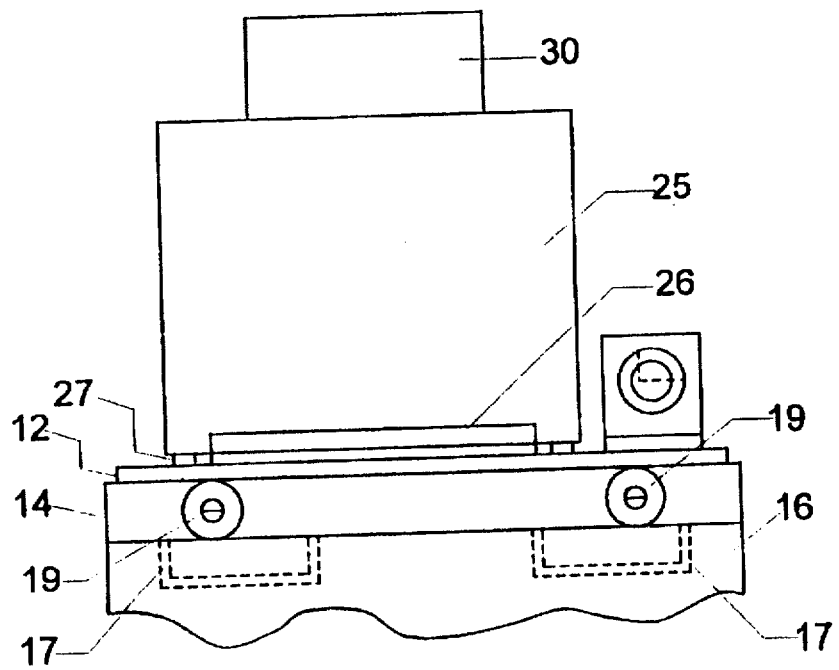
FIG. 2 is an end view of the FIG. 1 module.

FIG. 2 shows an end view of the FIG. 1 module with the protective case 16 removed. Referring now to both FIG. 1 and FIG. 2, a pair of channel members 17 (seen most clearly in FIG. 2) are arranged at the bottom side of base member 14. Channels 17 form pockets that are sized and spaced to accommodate the lifting forks of a fork lift. A plurality of retractable carrying handles 19 are provided at opposite ends of base member 14. Handles 19 comprise a rod member 20 arranged to slide outwardly within a sleeve 21 to the limit set by stop means 22. In an extended position (best shown in FIG. 3), rod 20 forms a convenient handle for men to lift and position the module or to carry it from place to place.

It is a practical requirement that the individual modules be arranged at a convenient working height after they have been interconnected for integrated operation. That may be done by placing module 10, and the other modules as well, on a bench or other support. However, it is preferred to shape and size each protective case 16 so that the case can be inverted to form a platform for its module. In this configuration, channels 17 fit inside the case, and base member 14 rests upon the bottom edges of the case sidewalls.

An analytical device 25 rests between rails 26, and is supported upon plate 12 by means of a plurality of resilient mounting blocks 27. Device 25, in one preferred embodiment, is a gas chromatograph equipped with a flow meter 29 and control console 30. A gas chromatograph is a device wherein a liquid sample is vaporized, and is passed through a chromatographic column with a carrier gas to separate the various components of the sample. The presence of sample components in the carrier gas stream emerging from the column is sensed by a detector that responds to the concentration of sample within the carrier gas. Nearly all detectors that are used at fixed-site laboratories can be placed onto the chromatograph 25. Appropriate detectors for use with chromatograph 25 include mass selective detectors, flame ionization detectors, thermal conductivity detectors, single or dual flame photometric detectors, and electron capture detectors. While analytical device 25 has been described as a gas chromatograph, other analytical devices may be substituted therefor. For example, device 25 may also be a high performance, liquid chromatograph; it may be a capillary zone electrophoresis instrument; a Fourier transform infrared spectrometer; or almost any other "fixed lab" analytical instrument.

Other auxiliary, or accessory, components may be incorporated within the analytical module. Those components may include a vacuum interface 32 and other accessories 33 and 34 depending upon the analytical needs to be met. Accessories 33 and 34 may comprise a thermal desorption apparatus for the analysis of volatile, airborne contaminants on solid sorbent tubes, or supplemental detector units for special purpose analyses that may be used with chromatograph 25. For example, if the compounds being analyzed include halogen atoms or polar functional groups, typical of many pesticides, then accessory detector 33 or 34 may usefully be an electron capture or coulometric detector. If positive identification of particular organic compounds is required, then the accessory detector may be a mass spectrometer.

Figure 3:
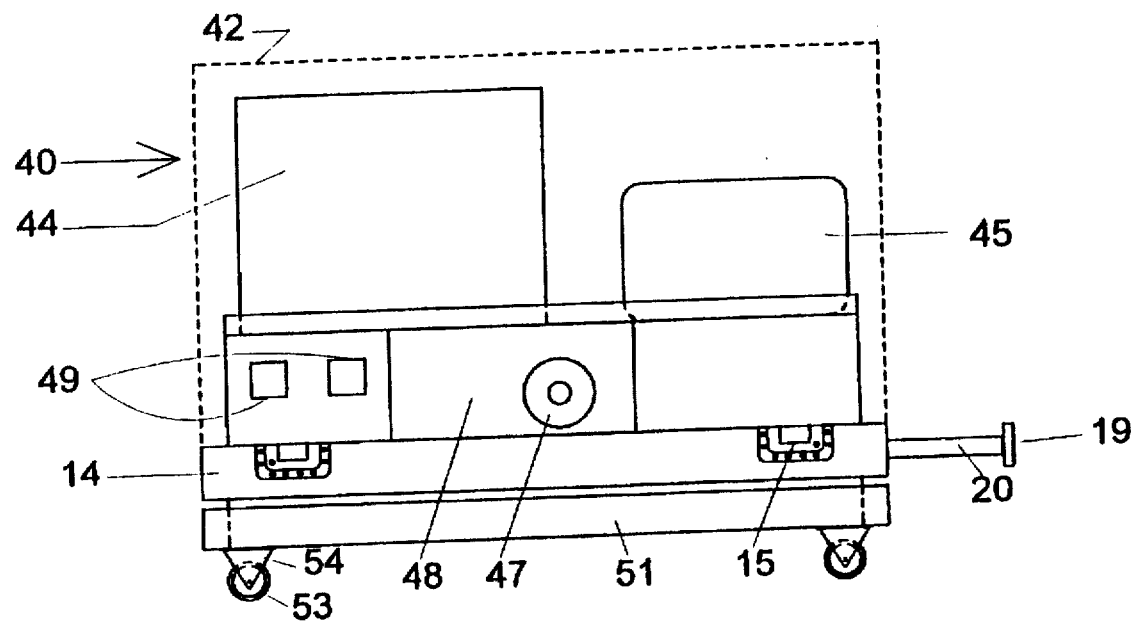
FIG. 3 is a generalized side view of a power module of this invention.

FIG. 3 is a generally schematic depiction of a power module 40 forming a part of the modular laboratory of this invention. Module 40 includes a base member 14 that is essentially identical to that of module 10, although it may be of somewhat different dimension. It includes locking hasps 15 for attachment of the base member to the protective case 16. The position of case 16, when in place on module 40, is shown in dotted outline 42. A plurality of handles 19 on rods 20, shown here in extended position, are provided for use in lifting and positioning the module.

In a preferred embodiment of this invention, there is also provided a wheeled base assembly arranged to fit as an integral adjunct to case 16 when the modules are made ready for shipping. That embodiment is best shown by reference to FIGS. 1 and 3 in combination. As shown in FIG. 1, a frame 51 having the same length and width as does case 16, is arranged to fit in a locking relationship at the top of that case. A castor 53, mounted in a swivel frame 54, is provided at each corner of frame 51. There is provided a square-set insert 56 at each upper corner of case 16 sized to accommodate the castors and their swivel frames. Frame 51 is detachable from the top of case 16 and its internal dimensions are sized such that channel members 17 nest therein. At the use site, the laboratory modules are prepared for operation by removing frame 51 from the top of case 16 and thereafter removing the case itself from the module base member 14. Channels 17, on the module bottom, are placed in a nesting relationship within the frame in the manner shown in FIG. 3. Each module, then, effectively becomes a cart that may be easily pushed from place to place.

Power module 40 includes an engine and generator assembly 44 of sufficient capacity to fill the needs of the laboratory. Those needs include power for operation of the analytical devices, as well as power to operate the support utilities and lighting. In most instances, a generating capacity of 5 to 7 kilowatts is adequate. It is preferred that the electricity generated by assembly 44 be of standard frequency and voltage so as to allow maximum use of stock components. A fuel tank 45 is provided to supply the engine that may be either a diesel or conventional gasoline engine. A muffler 47 and an air cleaning means 48 may be arranged below assembly 44. There is also provided a group of power outlets 49 arranged for interconnection to other laboratory modules through transmission cables (not shown).

Figure 4:
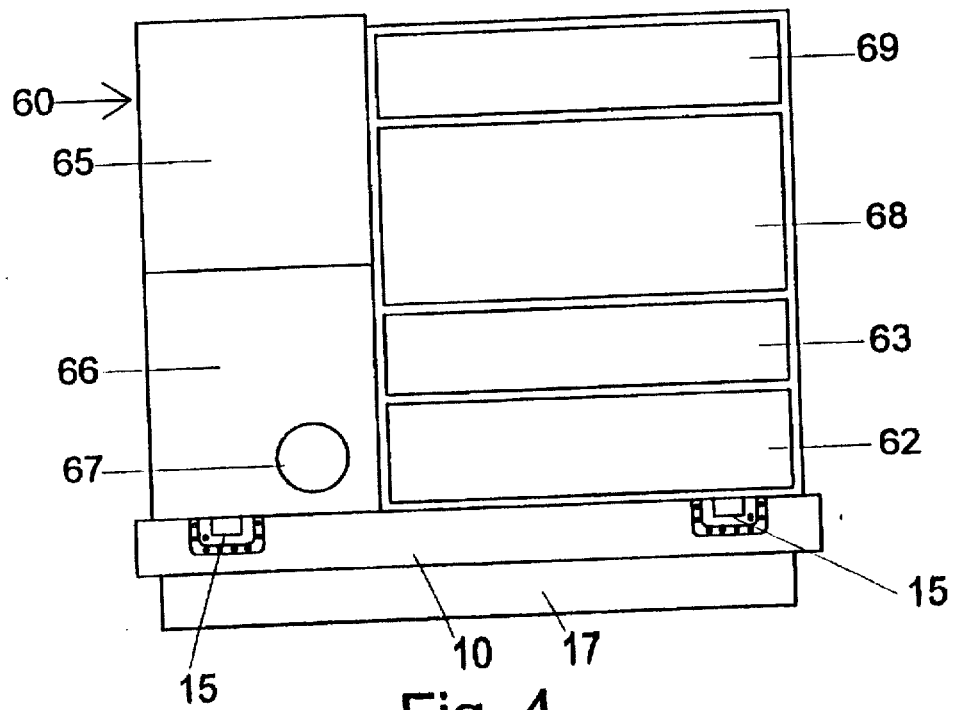
FIG. 4 is a side view of a utilities module that operates in cooperation with the analytical and power modules.

Referring now to FIG. 4, there is shown a service module 60 that is supplied by the power module and provides support to the analytical module. At a minimum, service module 60 includes a computer 62 and printer 63, together with means to generate and supply required gases to the analytical module. In the configuration shown, the gas generation means provided include means 65 to generate hydrogen, and means 66 to generate nitrogen and oxygen as well as purified air. Hydrogen generation means 65 preferably operates by the electrolysis of water; the electrical energy for the electrolysis being provided by the power module 40. Air is pulled into the module through port 67, and is circulated for cooling and to supply the nitrogen separation process. The air stream is purified and dried by filtration and adsorption and is compressed for use, or for the production of separate nitrogen and oxygen streams. Nitrogen and oxygen are preferably generated by their separation from air using a molecular sieve absorption process. Again, the energy to compress the air and to operate that separation process is supplied by the power module.

Service module 60 has in common with the analytical and service modules a base member 14 having channels 17 for fork lift access. As with the other modules, a protective case 16 (not shown) fits over the components mounted on the base and locks to that base through hasps 15. Any available space within the confines of the case 16 not taken up by other components of the service module is allocated for storage. A drawer 68 may be provided for manuals and a second compartment 69 finds use for spare parts storage.

By limiting each of the modules in size and weight so that they are shippable by commercial air freight, the laboratory can be readily and quickly transported to an airport nearest the site of use. The modules can then be loaded onto any available means of transport, using either manpower or fork lifts for the loadlifts for the loading operation, and moved directly to the use site. After arrival at the site, the protective cases are removed from each module, electrical power and gas interconnections between the modules are established, and the laboratory is ready for operation. It is preferred that all connections between the modules be color coded, and fitted with quick disconnects so that the modules can be easily and quickly interconnected and made ready for use once the modules arrive on site. In another preferred embodiment of the invention, the protective cases 16 of the modules, particularly case 16 of module 10, are sized and arranged so that the cases can be inverted and become platforms for operation of the modules.

A major advantage to the system of this invention as compared to prior art approaches is that it may be used in any of three configurations. It may be employed in a completely modular mode requiring only overhead shelter and a sufficiently conditioned environment to protect the equipment and operators from extremes of heat and cold. After being transported to a site in modules, the system may be easily converted to a mobile laboratory simply by installing the modules in a van or trailer. Finally, the modules may be used to form the nucleus of a fixed laboratory, requiring only floor space and normal support services. In any configuration, the modular laboratory of this invention significantly reduces quality control requirements for labs that have both mobile and fixed operations as the same analytical instrument can be used for both.

As may now be appreciated, this invention allows a sophisticated analytical laboratory to be brought to the site of need, rather than employing the usual procedures of taking samples for analysis at a remote location. It provides substantial operating advantages in any situation that requires the analysis of numerous samples for low level contaminant compounds. It will also be recognized by those skilled in this art that numerous modifications of the devices and techniques that have been described can be made without departing from the spirit and scope of the invention.

We claim:

1. A self contained, air transportable, analytical laboratory comprising:

a plurality of modules, each said module having a base member adapted for the mounting of components thereon, and a removable, protective case, each said case having an open bottom, closed side walls and a top, and arranged to lock to said base member to enclose said mounted components thereby forming a closed container for air transport of said module, said case sized and arranged so that, when inverted, said base member fits on the open bottom of said inverted case, said inverted case forming a platform to securely support said module during operation of said analytical laboratory; a first of said modules comprising an analytical device, and a second of said modules comprising an engine and generator assembly sized to produce sufficient electrical energy to power said first module; and means for operably interconnecting said modules.

2. The laboratory of claim 1 wherein said analytical device is a gas chromatograph.

3. The laboratory of claim 1 wherein said base member is supported upon a pair of parallel channels, said channels arranged to accept entry of the tines of a fork lift.

4. The laboratory of claim 1 wherein said base member includes a plurality of handles for lifting and carrying said module, each said handle retractable to a position that is flush with the case side walls when not in use.

5. The laboratory of claim 1 including a wheeled base assembly having a frame equal in length and width to said protective case, and having a castor at each corner thereof; said frame arranged to lock in place atop said case for shipment, and to be removable therefrom.

6. The laboratory of claim 5 wherein the frame is further arranged to cradle and support said pair of parallel channels and to thereby provide wheel means for said module.

7. The laboratory of claim 1 wherein the dimensions of each said case, when mounted on said base member, allow shipment of said module as commercial air cargo.

8. The laboratory of claim 7 wherein said base member is supported upon a pair of parallel channels, said channels arranged to accept entry of the times of a fork lift and to fit within said case when it is inverted and supporting said base member.

9. The laboratory of claim 1 including a third module, said third module comprising means for generating a gas for use by the analytical device of said first module, said gas selected from the group consisting of hydrogen, nitrogen, oxygen, and compressed air, said gas generation accomplished by employing electrical energy produced by said second module.

10. The laboratory of claim 9 wherein said gas is hydrogen, and wherein said third module comprises means of the electrolysis of water.

11. The laboratory of claim 9 wherein said gas is nitrogen, and wherein said third module comprises means for the separation of nitrogen from air.

* * * * *